United States Patent
Li et al.

(10) Patent No.: US 6,449,330 B1
(45) Date of Patent: Sep. 10, 2002

(54) METHODS AND APPARATUS FOR ARTIFACT REDUCTION IN COMPUTED TOMOGRAPHIC IMAGING

(75) Inventors: Jianying Li, New Berlin; Charles Shaughnessy, Whitefish Bay, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/681,939

(22) Filed: Jun. 28, 2001

(51) Int. Cl.$^7$ .................................................. A61B 6/03
(52) U.S. Cl. ............................ 378/4; 378/15; 378/901
(58) Field of Search ............................... 378/4, 15, 901

(56) References Cited

U.S. PATENT DOCUMENTS

| | | |
|---|---|---|
| 5,165,100 A | 11/1992 | Hsieh et al. |
| 5,237,524 A * | 8/1993 | Heinemann .................. 348/607 |
| 5,396,528 A | 3/1995 | Hu et al. |
| 5,416,815 A | 5/1995 | Hsieh |
| 5,533,091 A | 7/1996 | Hsieh |
| 5,727,041 A | 3/1998 | Hsieh |
| 5,812,628 A | 9/1998 | Hsieh |
| 5,818,896 A * | 10/1998 | Hsieh .......................... 378/15 |
| 5,832,055 A * | 11/1998 | Dewaele ...................... 250/587 |
| 6,009,140 A | 12/1999 | Hsieh |
| 6,035,012 A | 3/2000 | Hsieh |
| 6,061,419 A | 5/2000 | Hsieh et al. |
| 6,115,487 A | 9/2000 | Toth et al. |
| 6,134,292 A | 10/2000 | Hsieh |
| 6,215,841 B1 | 4/2001 | Hsieh |
| 6,233,308 B1 | 5/2001 | Hsieh |

FOREIGN PATENT DOCUMENTS

| | | |
|---|---|---|
| DE | 100 43 725 A1 | 9/1999 |
| EP | 1 104 917 A2 | 6/2001 |

OTHER PUBLICATIONS

U.S. patent application No. 09/810,925 filed Mar. 16, 2001.

* cited by examiner

Primary Examiner—David V. Bruce
(74) Attorney, Agent, or Firm—Carl B. Horton, Esq.; Armstrong Teasdale LLP

(57) ABSTRACT

A method for reducing artifacts in computed tomographic (CT) images is provided that is particularly useful for CT applications requiring higher gantry rotation rates. The method includes selecting a set of thresholds for projection view data; utilizing a smoothing kernel in accordance with the selected set of thresholds to produce a set of smoothed projections from a set of original projections obtained from a scan of an object, wherein an amount of smoothing applied varies depending upon a relationship of the original projections to the thresholds; producing a set of final projections utilizing the set of original projections and the set of smoothed projections; and reconstructing images of the object utilizing the final projections.

38 Claims, 2 Drawing Sheets

METHODS AND APPARATUS FOR ARTIFACT REDUCTION IN COMPUTED TOMOGRAPHIC IMAGING

BACKGROUND OF INVENTION

This invention relates generally to computed tomographic (CT) imaging methods and apparatus, and more particularly to methods and apparatus for reducing artifacts in computed tomographic imaging systems such as those used for medical imaging.

In recent computed tomographic (CT) imaging systems, scan speeds have been increased to sub-second gantry rotations to reduce patient motion, enable new applications, and to increase patient throughput. However, because of x-ray tube power limitations, x-ray currents cannot be kept as constant as at slower scan speeds, often causing image artifacts to be created. These artifacts appear in the images as noise and streaking, which are related to the generally lower signals levels available at higher gantry speeds. Corrections have been applied based upon a single signal threshold level to reduce image noise and streaking artifacts to some extent. However, there remain areas in which signals are slightly higher than the single threshold but for which corrections are still required. In addition, there remain areas in which a greater correction is needed than can be provided with such corrections. As a result, residual streaking artifacts often exist in images processed using this artifact reduction method.

SUMMARY OF INVENTION

Therefore, in one aspect of the present invention, a method for reducing artifacts in computed tomographic (CT) images is provided that is particularly useful for CT applications requiring higher gantry rotation rates. The method includes selecting a set of thresholds for projection view data; utilizing a smoothing kernel in accordance with the selected set of thresholds to produce a set of smoothed projections from a set of original projections obtained from a scan of an object, wherein an amount of smoothing applied varies depending upon a relationship of the original projections to the thresholds; producing a set of final projections utilizing the set of original projections and the set of smoothed projections; and reconstructing images of the object utilizing the final projections.

In another aspect of the present invention, there is provided a method for reducing artifacts in CT images that includes utilizing clinical image studies to select a set of thresholds, including thresholds T1, T2, and T3, for projection data, in accordance with a desired image resolution and noise, utilizing a smoothing kernel in accordance with the selected set of thresholds to produce a set of smooth projections from a set of original projections obtained from a scan of an object, wherein an amount of smoothing applied varies depending upon a relationship of the original projections to the thresholds; producing a set of final projections utilizing the set of original projections and the set of smoothed projections; and reconstructing at least one image of the object utilizing the final projections.

In yet another aspect of the present invention, there is provided a CT imaging system configured to acquire a set of original projections of an object; utilize a smoothing kernel to produce a set of smoothed projections from the set of original projections, wherein an amount of smoothing applied varies depending upon a relation of the original projections to the thresholds; produce a set of final projections utilizing the set of original projections and the set of smoothed projections; and reconstruct at least one image of the object utilizing the set of final projections.

In still another aspect of the present invention, there is provided a CT imaging system configured to: acquire a set of original projections; utilize a smoothing kernel in accordance with a selected set of thresholds T1, T2, and T3 to produce a set of smoothed projections from the set of original projections, wherein an amount of smoothing applied varies depending upon a relationship of the original projections to the thresholds; produce a set of final projections utilizing the set of original projections and the set of smoothed projections; and reconstruct images of the object utilizing the set of final projections, wherein the smoothing kernel is a three-point kernel for views that are below T1 but greater than T2, a five-point smoothing kernel for views that are below T2 but greater than T3, and a nine-point kernel for views that are below T3.

In yet another aspect of the present invention, there is provided a processor for reducing artifacts in scanned images. The processor is configured to: utilize a smoothing kernel in accordance with a selected set of thresholds to produce a set of smoothed projections from a set of original projections obtained from a scan of an object, wherein an amount of smoothing applied varies depending upon a relationship of the original projections to the thresholds; produce a set of final projections utilizing the set of original projections and the set of smoothed projections; and reconstruct an image of the object utilizing the final projections.

In still another aspect of the present invention, there is provided a processor for reducing artifacts in scanned images. The processor is configured to: utilize a smoothing kernel in accordance with a selected set of thresholds T1, T2, and T3, to produce a set of smoothed projections from a set of original projections obtained from a scan of an object, wherein an amount of smoothing applied varies depending upon a relationship of the original projections to the thresholds; producing a set of final projections utilizing the set of original projections and the set of smoothed projections; and reconstructing images of the object utilizing the final projections, wherein the smoothing kernel is a 3-point kernel for views that are below T1 but greater than T2, a 5-point kernel for views that are below T2 but greater than T3, and a 9-point kernel for views that are below T3.

In another aspect of the present invention, there is provided a computer-readable medium having recorded thereon instructions configured to instruct a processor to: utilize a smoothing kernel in accordance with a selected set of thresholds to produce a set of smoothed projections from a set of original projections obtained from a scan of an object, wherein an amount of smoothing applied varies depending upon a relationship of the original projections to the thresholds; produce a set of final projections utilizing the set of original projections and the set of smoothed projections; and reconstruct an image of the object utilizing the final projections.

And in yet another aspect of the present invention, there is provided A computer-readable medium having recorded thereon instructions configured to instruct a processor to: utilize a smoothing kernel in accordance with a selected set of thresholds T1, T2, and T3, to produce a set of smoothed projections from a set of original projections obtained from a scan of an object, wherein an amount of smoothing applied varies depending upon a relationship of the original projections to the thresholds; produce a set of final projections utilizing the set of original projections and the set of smoothed projections; and reconstruct images of the object utilizing the final projections, wherein the smoothing kernel is a 3-point kernel for views that are below T1 but greater than T2, a 5-point kernel for views that are below T2 but greater than T3, and a 9-point kernel for views that are below T3.

The above-described embodiments of the present invention are useful in reducing image noise and streaking compared to previously known artifact reduction methods, while retaining image resolution and sharpness. Thus, embodiments of the invention can be advantageously used in situations in which faster scans and/or lower dose scans are required.

DETAILED DESCRIPTION

Figure 1:
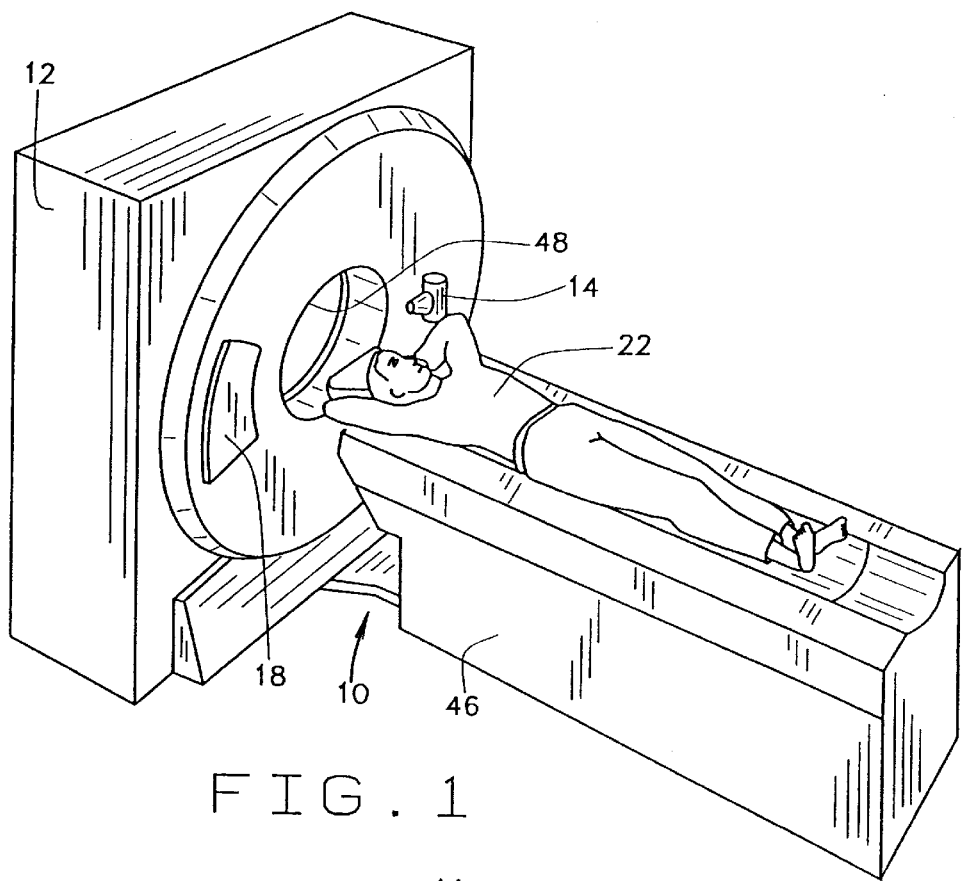
FIG. 1 is a pictorial view of a CT imaging system embodiment.
Figure 2:
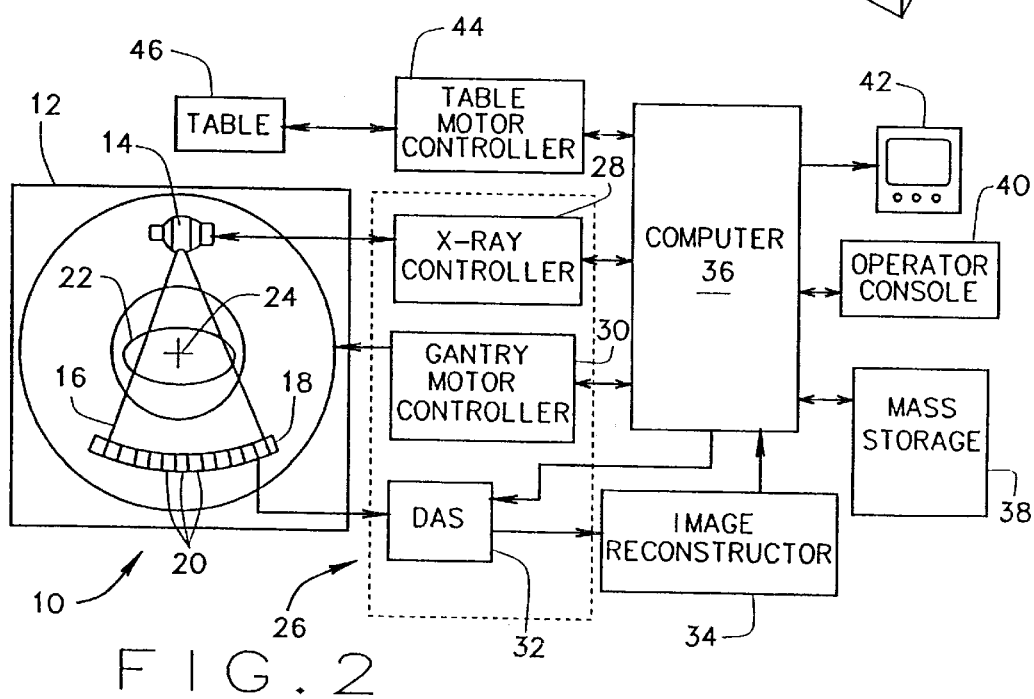
FIG. 2 is a block schematic diagram of the system illustrated in FIG. 1.

In one embodiment and referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 (or another suitable type of display) allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

To reduce artifacts in a signal-independent manner, image reconstructor 34 in one embodiment of the present invention reconstructs images utilizing a set of threshold values for projection views in scan data. The set of threshold values includes more than one threshold, and, in one embodiment, includes three threshold values. The thresholds are selected 50 based upon a study of clinical images. In one embodiment, one of the selected thresholds is greater and one of the selected thresholds is smaller than a threshold selected for use with the previously-known single-threshold method. This selection of thresholds reduces residual noise and streaking artifacts and provides stronger correction for signals that are extremely low. To minimize adverse effects of smoothing and artifact correction on image resolution and sharpness, different sets of smoothing kernels are associated 52 with the different thresholds. Less smoothing (i.e., shorter kernels) is applied to the highest threshold, and stronger smoothing (longer smoothing kernels) is applied to the smaller threshold. Thus, a smoothing kernel is used in accordance with the selected set of threshold to produce a set of smoothed projections from a set of original projections. The amount of smoothing varies depending upon the relationship of the original projections (i.e., the data comprising the original projections) to the thresholds.

In one exemplary embodiment, a set of three thresholds (T1, T2, and T3) are selected using clinical image studies, in accordance with a compromise between image resolution and noise.

A scan 54 of an object 22 is performed utilizing CT system 10 to collect scan data, including projection views. In one embodiment of the present invention, the projection views are processed by image reconstructor 34, which performs functions 56, 58, 60, 62, and 64 described below. However, in another embodiment, these functions are performed in a stand-alone processor on scan data collected by imaging system 10.

Smoothing 56 of projection data is performed with a 3-point kernel for views that are below T1 but greater than T2; with a 5-point kernel for views that are below T2 but greater than T3; and with a 9-point kernel for views that are below T3. Thus, a set of smoothed projections (i.e., projection views) is obtained.

Error projections are formed by subtracting 58 the smoothed projection views from the original projection views.

The error projections are then multiplied 60 by a signal-dependent smoothing gain to produce smoothed error projections.

Final projections are formed by subtracting 62 the smoothed error projections from the corresponding original projections.

Figure 3:
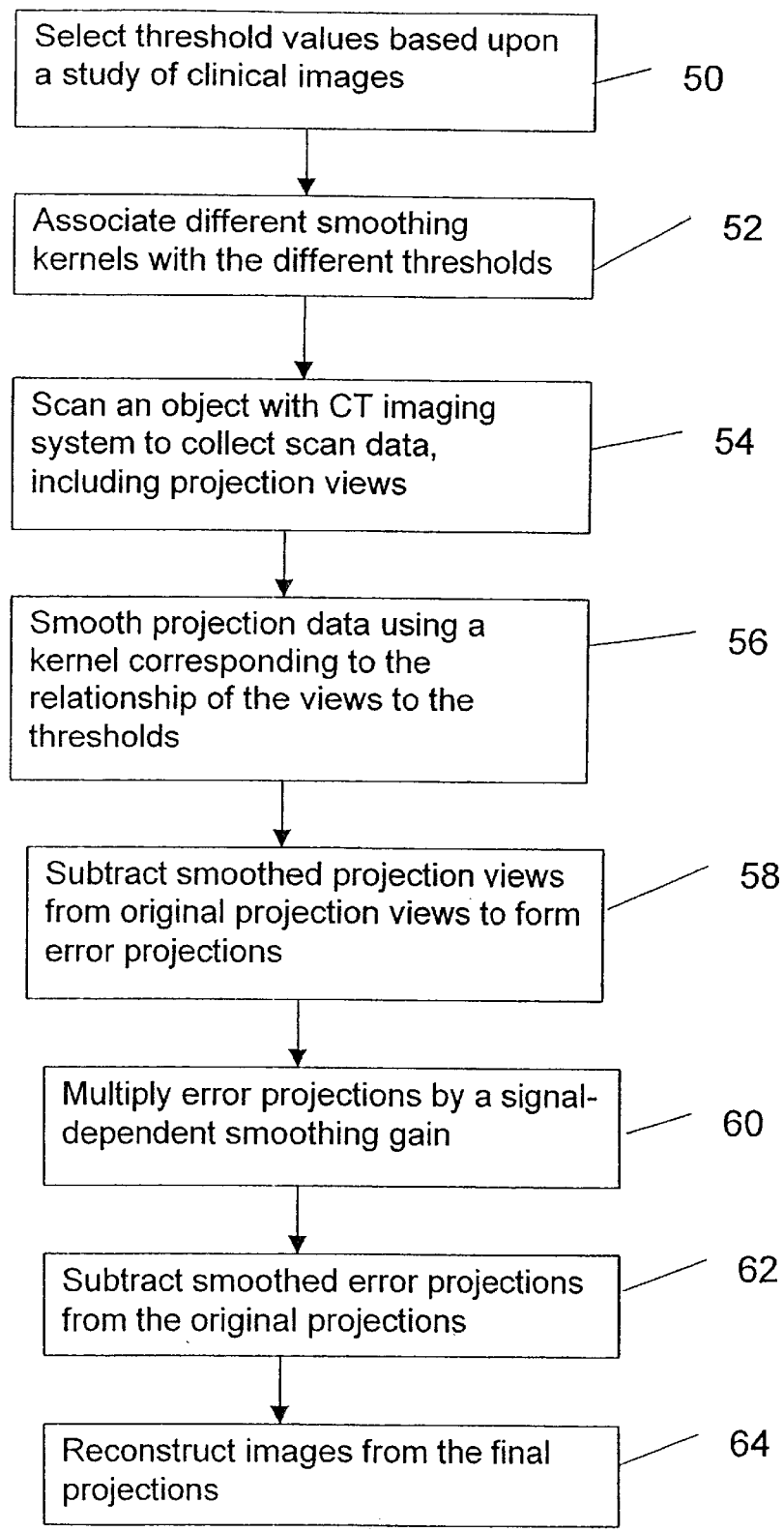
FIG. 3 is a flow chart of one embodiment of the present invention.

The final projections are used to reconstruct 64 images suitable for display on cathode ray tube 42 or another display device. Smoothing 56, subtracting 58, multiplication 60, and subtracting 62 are repeated for each of the angular views. The serial loop implementation represented in FIG. 3 may be replaced, as a design choice, by an equivalent implementation having more parallelism.

In tests performed on patient scan data, reduced image noise and streaking were observed compared to previously known artifact reduction methods, while image resolution and sharpness was found to be close to that of the images produced by the previously-known methods. Thus, embodiments of the invention will be found useful in situations where faster scans and/or lower dose scans are required.

The present invention has been described by reference to a CT imaging system 10, in which ample computing power resides in a "processor" (e.g., one or more of image reconstructor 34 and computer 36) to perform the data computations described herein. However, in another embodiment, the processor resides in a different type of scanning imaging system. In one embodiment, the processor is separate from the imaging system, and inputs projections obtained from a separate scanning imaging system. Thus, scanning an object or patient 22 with an imaging system 10 can produce projection data that can be stored and later used in such a processor. Both CT imaging system embodiments and other processor embodiments can be provided with media readers, such as diskette drives and CD-ROM drives, that read computer-readable media having encoded instructions thereon for performing the methods and processes described.

The indefinite articles "a" or "an" preceding an element or step in the description or claims presented herein are intended to refer to one or more of the named elements or steps, unless such meaning is explicitly excluded. In addition, features described in connection with "one embodiment of the present invention," should not be understood as implying that those features may not be found in other embodiments of the present invention.

While the invention has been described in terms of various specific embodiments, those skilled in the art will recognize that the invention can be practiced with modification within the spirit and scope of the claims.

What is claimed is:

1. A method for reducing artifacts in computed tomographic (CT) images, comprising:
    selecting a set of thresholds for projection data;
    utilizing a smoothing kernel in accordance with the selected set of thresholds to produce a set of smoothed projections from a set of original projections obtained from a scan of an object, wherein an amount of smoothing applied varies depending upon a relationship of the original projections to the thresholds;
    producing a set of final projections utilizing the set of original projections and the set of smoothed projections; and
    reconstructing at least one image of the object utilizing the final projections.

2. A method in accordance with claim 1 wherein said producing a set of final projections comprises subtracting the smoothed projections from corresponding original projections to produce a set of error projections.

3. A method in accordance with claim 2 wherein said producing a set of final projections further comprises multiplying the error projections by a signal-dependent smoothing gain to produce a set of smoothed error projections.

4. A method in accordance with claim 3 wherein said producing a set of final projections further comprises subtracting the smoothed error projections from corresponding said original projections to produce the set of final projections.

5. A method in accordance with claim 4 and further comprising acquiring the original projections with a CT imaging system, and utilizing a processor of the CT imaging system to produce the set of smoothed projections, to subtract the smoothed projections from the corresponding original projections, to multiply the error projections by the signal-dependent smoothing gain, and to subtract the smoothed error projections from the corresponding original projections.

6. A method in accordance with claim 1 wherein said selecting a set of thresholds comprises selecting three thresholds T1, T2, and T3.

7. A method in accordance with claim 6 wherein said selecting a set of thresholds comprises utilizing clinical image studies to select the three thresholds in accordance with a desired image resolution and noise.

8. A method for reducing artifacts in computed tomographic (CT) images, comprising:
    utilizing clinical image studies to select a set of thresholds, including thresholds T1, T2, and T3, for projection data, in accordance with a desired image resolution and noise;
    utilizing a smoothing kernel in accordance with the selected set of thresholds to produce a set of smoothed projections from a set of original projections obtained from a scan of an object, wherein an amount of smoothing applied varies depending upon a relationship of the original projections to the thresholds;
    producing a set of final projections utilizing the set of original projections and the set of smoothed projections; and
    reconstructing at least one image of the object utilizing the final projections, wherein the smoothing kernel is a 3-point kernel for views that are below T1 but greater than T2, a 5-point kernel for views that are below T2 but greater than T3, and a 9-point kernel for views that are below T3.

9. A method in accordance with claim 8 wherein said producing a set of final projections comprises subtracting the smoothed projections from corresponding said original projections to produce a set of error projections.

10. A method in accordance with claim 9 wherein said producing a set of final projections further comprises multiplying the error projections by a signal-dependent smoothing gain to produce a set of smoothed error projections.

11. A method in accordance with claim 9 wherein said producing a set of final projections further comprises subtracting the smoothed error projections from corresponding said original projections to produce the set of final projections.

12. A computed tomographic (CT) imaging system configured to:
    acquire a set of original projections of an object;
    utilize a smoothing kernel in accordance with a selected set of thresholds to produce a set of smoothed projections from said set of original projections, wherein an amount of smoothing applied varies depending upon a relationship of said original projections to said thresholds;
    produce a set of final projections utilizing said set of original projections and said set of smoothed projections; and
    reconstruct at least one image of the object utilizing said set of final projections.

13. A CT imaging system in accordance with claim 12, wherein to produce said set of final projections, said CT imaging system is configured to subtract said smoothed projections from corresponding said original projections to produce a set of error projections.

14. A CT imaging system in accordance with claim 13 wherein to produce said set of final projections, said CT imaging system is further configured to multiply said error projections by a signal-dependent smoothing gain to produce a set of smoothed error projections.

15. A CT imaging system in accordance with claim 14 wherein to produce said set of final projections, said CT imaging system is further configured to subtract said smoothed error projections from corresponding said original projections to produce said set of final projections.

16. A CT imaging system in accordance with claim 12 wherein said selected set of thresholds comprise three thresholds, T1, T2, and T3.

17. A computed tomographic (CT) imaging system configured to:
   acquire a set of original projections;
   utilize a smoothing kernel in accordance with a selected set of thresholds T1 T2, and T3 to produce a set of smoothed projections from said set of original projections, wherein an amount of smoothing applied varies depending upon a relationship of said original projections to said thresholds;
   produce a set of final projections utilizing said set of original projections and said set of smoothed projections; and
   reconstruct at least one image of the object utilizing said set of final projections;
   wherein said smoothing kernel is a 3-point kernel for views that are below T1 but greater than T2, a 5-point kernel for views that are below T2 but greater than T3, and a 9-point kernel for views that are below T3.

18. A CT imaging system in accordance with claim 17 wherein to produce said set of final projections, said CT imaging system is configured to subtract said smoothed projections from corresponding said original projections to produce a set of error projections.

19. A CT imaging system in accordance with claim 18 wherein to produce said set of final projections, said CT imaging system is further configured to multiply said error projections by a signal-dependent smoothing gain to produce a set of smoothed error projections.

20. A CT imaging system in accordance with claim 19 wherein to produce said set of final projections, said CT imaging system is further configured to subtract said smoothed error projections from corresponding said original projections to produce said set of final projections.

21. A processor for reducing artifacts in scanned images, said processor configured to:
   utilize a smoothing kernel in accordance with a selected set of thresholds to produce a set of smoothed projections from a set of original projections obtained from a scan of an object, wherein an amount of smoothing applied varies depending upon a relationship of the original projections to said thresholds;
   produce a set of final projections utilizing the set of original projections and said set of smoothed projections; and
   reconstruct an image of the object utilizing said final projections.

22. A processor in accordance with claim 21 wherein to produce said set of final projections, said processor is configured to subtract said smoothed projections from corresponding projections of the original projections to produce a set of error projections.

23. A processor in accordance with claim 22 wherein to produce a set of final projections, said processor is further configured to multiply said error projections by a signal-dependent smoothing gain to produce a set of smoothed error projections.

24. A processor in accordance with claim 23 wherein to produce a set of final projections, said processor is further configured to subtract said smoothed error projections from corresponding projections of the original projections to produce said set of final projections.

25. A processor in accordance with claim 21 wherein said set of thresholds comprises three thresholds T1, T2, and T3.

26. A processor for reducing artifacts in scanned images, said processor configured to:
   utilize a smoothing kernel in accordance with a selected set of thresholds T1, T2, and T3, to produce a set of smoothed projections from a set of original projections obtained from a scan of an object, wherein an amount of smoothing applied varies depending upon a relationship of the original projections to said thresholds;
   producing a set of final projections utilizing the set of original projections and said set of smoothed projections; and
   reconstructing images of the object utilizing said final projections, wherein said smoothing kernel is a 3-point kernel for views that are below T1 but greater than T2, a 5-point kernel for views that are below T2 but greater than T3, and a 9-point kernel for views that are below T3.

27. A processor in accordance with claim 26 wherein to produce a set of final projections, said processor is configured to subtract said smoothed projections from corresponding projections of the original projections to produce a set of error projections.

28. A processor in accordance with claim 27 wherein to produce a set of final projections, said processor is further configured to multiply said error projections by a signal-dependent smoothing gain to produce a set of smoothed error projections.

29. A processor in accordance with claim 27 wherein to produce a set of final projections, said processor is further configured to subtract said smoothed error projections from corresponding projections of the original projections to produce said set of final projections.

30. A computer-readable medium having recorded thereon instructions configured to instruct a processor to:
   utilize a smoothing kernel in accordance with a selected set of thresholds to produce a set of smoothed projections from a set of original projections obtained from a scan of an object, wherein an amount of smoothing applied varies depending upon a relationship of the original projections to said thresholds;
   produce a set of final projections utilizing the set of original projections and said set of smoothed projections; and
   reconstruct an image of the object utilizing said final projections.

31. A computer-readable medium in accordance with claim 30 wherein to produce said set of final projections, said processor is configured to subtract said smoothed projections from corresponding projections of the original projections to produce a set of error projections.

32. A computer-readable medium in accordance with claim 31 wherein to produce a set of final projections, said computer-readable medium has encoded thereon instructions configured to instruct the processor to multiply said error projections by a signal-dependent smoothing gain to produce a set of smoothed error projections.

33. A computer-readable medium in accordance with claim 32 wherein to produce a set of final projections, said computer-readable medium has encoded thereon instructions configured to instruct the processor to subtract said smoothed error projections from corresponding projections of the original projections to produce said set of final projections.

34. A computer-readable medium in accordance with claim 30 wherein said set of thresholds comprises three thresholds T1, T2, and T3.

35. A computer-readable medium having recorded thereon instructions configured to instruct a processor to:

utilize a smoothing kernel in accordance with a selected set of thresholds T1, T2, and T3, to produce a set of smoothed projections from a set of original projections obtained from a scan of an object, wherein an amount of smoothing applied varies depending upon a relationship of the original projections to said thresholds;

produce a set of final projections utilizing the set of original projections and said set of smoothed projections; and reconstruct images of the object utilizing said final projections, wherein said smoothing kernel is a 3-point kernel for views that are below T1 but greater than T2, a 5-point kernel for views that are below T2 but greater than T3, and a 9-point kernel for views that are below T3.

36. A computer-readable medium in accordance with claim 35 wherein to produce a set of final projections, said computer-readable medium has encoded thereon instructions configured to instruct the processor to subtract said smoothed projections from corresponding projections of the original projections to produce a set of error projections.

37. A computer-readable medium in accordance with claim 36 wherein to produce a set of final projections, said computer-readable medium has encoded thereon instructions configured to instruct the processor to multiply said error projections by a signal-dependent smoothing gain to produce a set of smoothed error projections.

38. A computer-readable medium in accordance with claim 36 wherein to produce a set of final projections, said computer-readable medium has encoded thereon instructions configured to instruct the processor to subtract said smoothed error projections from corresponding projections of the original projections to produce said set of final projections.

* * * * *

UNITED STATES PATENT AND TRADEMARK OFFICE
CERTIFICATE OF CORRECTION

PATENT NO. : 6,449,330 B1
DATED : September 10, 2002
INVENTOR(S) : Li et al.

It is certified that error appears in the above-identified patent and that said Letters Patent is hereby corrected as shown below:

Column 7,
Line 8, delete "T1 T2, and T3" and insert therefor -- T1, T2, and T3 --.

Signed and Sealed this

Eighteenth Day of February, 2003

JAMES E. ROGAN
*Director of the United States Patent and Trademark Office*